United States Patent [19]

Sasaoka et al.

[11] Patent Number: 5,070,194
[45] Date of Patent: Dec. 3, 1991

[54] METHOD FOR PRODUCTION OF β-LACTAM DERIVATIVES

[75] Inventors: Michio Sasaoka; Nori Saito; Takashi Shiroi, all of Tokushima; Shigemitsu Nagao, Mobara; Ryo Kikuchi; Yutaka Kameyama, both of Tokushima, all of Japan

[73] Assignee: Otsuka Kagaku Kabushiki Kaisha, Osaka, Japan

[21] Appl. No.: 333,403

[22] Filed: Apr. 5, 1989

Related U.S. Application Data

[63] Continuation-in-part of Ser. No. 21,058, Jan. 6, 1987, abandoned.

[51] Int. Cl.$^5$ ............................................. C07D 499/08
[52] U.S. Cl. ..................... 540/214; 540/222; 540/225; 540/227; 540/300; 540/301; 540/310; 540/318
[58] Field of Search ............... 540/301, 300, 227, 214, 540/225, 222, 318, 310

[56] References Cited

U.S. PATENT DOCUMENTS 4,925,934  5/1990  Taniguchi et al. .................. 540/310

Primary Examiner—Nicholas S. Rizzo
Attorney, Agent, or Firm—Armstrong, Nikaido, Marmelstein, Kubovcik & Murray

[57] ABSTRACT

This invention provides a method of producing a β-lactam derivative represented by the formula (I):

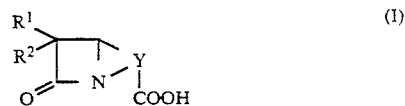

said method consisting essentially of the step of reacting a β-lactam derivative represented by the formula (II):

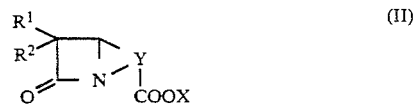

with a phenol in a reaction system which consists essentially of said β-lactam derivative of formula (II) and said phenol.

6 Claims, No Drawings

METHOD FOR PRODUCTION OF β-LACTAM DERIVATIVES

This application is a continuation-in-part of application Ser. No. 021,058, filed Jan. 6, 1987, now abandoned.

TECHNICAL FIELD

The present invention relates to a method for production of β-lactam derivatives.

BACKGROUND ART

β-Lactam derivatives used as antibiotics generally have carboxyl groups within their molecules and, in many instances, are put to use as the free carboxylic acids or with the carboxyl groups protected in the form of pharmaceutically acceptable salts. However, in the process of synthesis of β-lactam antibiotics, such carboxyl groups are usually protected with suitable protective groups, which must be ultimately eliminated in good yield without affecting the other moiety of the molecule.

A β-lactam derivative having a protected carboxyl group may be represented by the general formula:

wherein $R^1$ is a hydrogen atom, a lower alkoxy group or a formamido group; $R^2$ is a hydrogen atom, a halogen atom, an amino group, an amido group or an imido group;

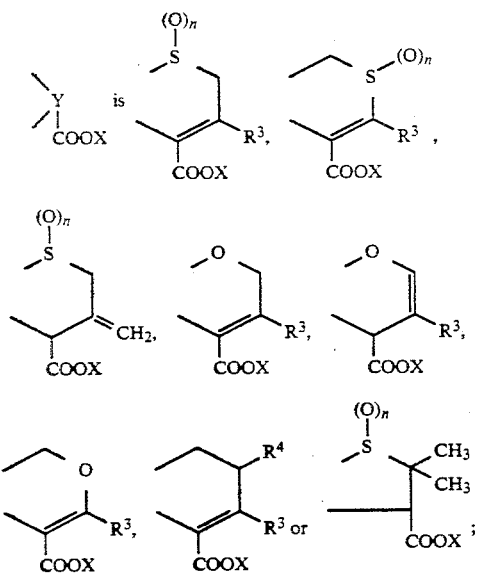

$R^3$ is a hydrogen atom, a hydroxyl group, a halogen atom, a lower alkoxyl group, a substituted or unsubstituted vinyl group, a lower alkoxymethyl group, acetoxymethyl group, carbamoyloxymethyl group, a heterocyclethiomethyl group, 5-methyltetrazol-2-ylmethyl group, 1-methylpyrrolidinomethyl group or pyridiniummethyl group; $R^4$ is a hydrogen atom, a hydroxyl group, a halogen atom, a lower alkoxyl group, a lower acyloxyl group, a lower alkylthio group or a heterocycle-thio group; n is 0, 1 or 2; and X is selected from the group consisting of a benzyl group having a hydroxyl group, a lower alkyl group or a lower alkoxy group as a phenyl ring substituent, a diphenylmethyl group, a diphenylmethyl group having a hydroxyl group, a lower alkyl group or a lower alkoxy group as a phenyl ring substituent, or tert-butyl. Heretofore elimination of the carboxyl-protecting group X from the β-lactam derivative to give a β-lactam derivative of the general formula:

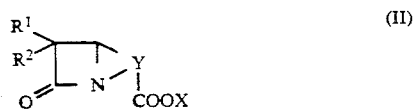

wherein $R^1$ and $R^2$ are as defined above,

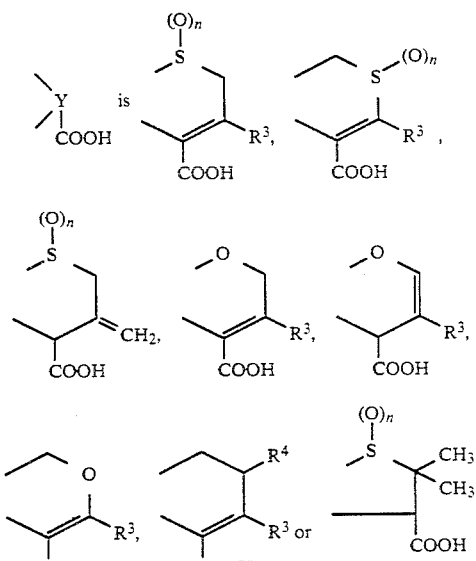

is accomplished by subjecting the β-lactam derivative of general formula (II) to catalytic reduction using a noble metal catalyst or to treatment with an acid, for instance. The latter method includes such versions as one using trifluoroacetic acid (Journal of The American Chemical Society 91, 5674, 1969), one using formic acid (Chemical Pharmaceutical Bulletin 30, 4545, 1982), the method in which the starting compound is reacted with aluminum chloride in the presence of anisole (Tetrahedron Letters 2793, 1979) and so on. However, these prior art methods have the following disadvantages.

Referring, first, to the catalytic reduction using a noble metal catalyst, β-lactam antibiotics generally contain a sulfide bond which may act as a catalyst poison and, therefore, the expensive noble metal catalyst must be used in a large amount. Furthermore, this method cannot be applied to β-lactam antibiotics containing reducible groups such as nitro, a carbon-to-carbon multiple bond or the like. Moreover, when the protective group is a tert-butyl group, it cannot be eliminated by this method. Further, when the protective group is a benzyl group having a hydroxy group, a lower alkyl group or a lower alkoxy group as a phenyl ring substituent or a diphenylmethyl group having a hydroxy group, a lower alkyl group or a lower alkoxy group as a phenyl ring substituent, this method fails to eliminate these groups in many instances.

The method using an acid also has the disadvantage that it requires at least a stoichiometric amount of strong acid despite the fact that the β-lactam derivative of general formula (I) is unstable to acid, with the result that the β-lactam derivative of general formula (I) once produced by the method is decomposed to detract from its ultimate yield.

For example, when a p-methoxybenzyl group masking the carboxyl group of cephalosporin compound of the formula (III) given below is to be eliminated with trifluoroacetic acid, this expensive reagent trifluoroacetic acid must be used generally in an amount of at least 5 molar equivalents relative to the cephalosporin compound of general formula (III). With an equimolar amount of trifluoroacetic acid, for instance, the above reaction does not substantially proceed. Suppose that the cephalosporin of formula (III) were deprotected with a large amount of trifluoroacetic acid and, after the reaction, one tried to recover the triflurroacetic acid for reuse, a substantial loss of the acid would be inevitable. Furthermore, in the course of the recovery procedure, the acid-labile compound of the following formula (IV) would be decomposed to further detract from the reaction yield.

It is, thus, clear that there is not available a method by which a carboxyl-protecting group X can be eliminated from a carboxy-protected β-lactam derivative of general formula (II) to give a β-lactam derivative of general formula (I) in good yield and without difficulties on a commercial scale.

DISCLOSURE OF INVENTION

The present invention provides a method by which a carboxyl-protecting group X can be eliminated from a carboxy-protected β-lactam derivative of general formula (II) to give a β-lactam derivative of general formula (I) in good yield and without difficulties on a commercial scale.

Thus, the present invention relates to a method of producing a β-lactam derivative characterized by reacting a carboxy-protected β-lactam derivative of general formula (II) with a phenol compound to give a β-lactam derivative of general formula (I).

In the formulae (I) and (II), $R^1$ may be a hydrogen atom, a lower alkoxy group such as methoxy, ethoxy, etc., and a formamido group.

Examples of $R^2$ include a hydrogen atom, a halogen atom, an amino group, an amido group, an imido group and so on. The halogen atom mentioned just above may for example be fluorine, chlorine, bromine or iodine. As

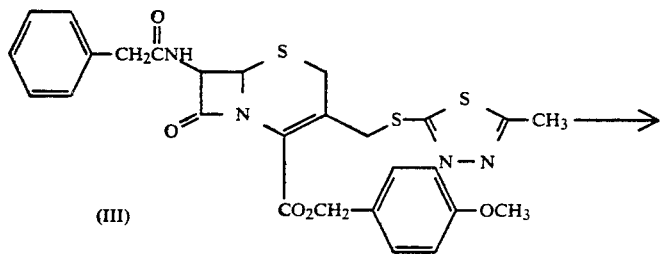

(III)

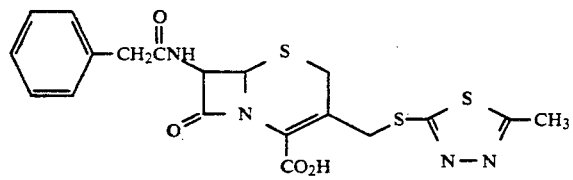

(IV)

The method employing formic acid also has a similar disadvantage. Thus, the expensive reagent formic acid of 98 to 100% concentration must be used in large excess as a reaction solvent. And if vacuum distillation, for instance, be carried out for its recovery and reuse, the acid-labile compound of the above formula (IV) would be decomposed to detract from its yield.

The method which comprises reacting the protected compound with aluminum chloride in the presence of anisole has the following disadvantages. It is essential to use aluminum chloride which, however, is difficult to handle because it tends to undergo exothermic reaction with atmospheric moisture to give rise to hydrochloric acid. Furthermore, as the reaction mixture is rendered strongly acidic during the reaction or the subsequent workup procedure, the acid-labile compound of general formula (IV) is decomposed so that the yield of the compound is adversely affected. In addition, in the workup procedure after the reaction, a large amount of aluminum hydroxide must be disposed of.

examples of said amido group, there may be mentioned benzamido, phenylacetamido, phenoxyacetamido, phenylglycylamido, amino-protected phenylglycylamido, p-hydroxyphenylglycylamido, hydroxy- and amino-protected p-hydroxyphenylglycylamido, thiolacetamido, α-carboxyphenylacetamido, carboxy-protected α-carboxyphenylacetamido, α-hydroxyphenylacetamido, hydroxy-protected α-hydroxyphenylacetamido, 2-(2-amino-4-thiazolyl)-2-methoxyiminoacetamido, amino-protected 2-(2-amino-4-thiazolyl)-2-methoxyiminoacetamido, 2-(2-furyl)-2-methoxyiminoacetamido, 2-(2-amino-4-thiazolyl)-2-(carboxymethoxyimino)acetamido, amino- and carboxy-protected 2-(2-amino-4-thiazolyl)-2-(carboxymethoxyimino)acetamido, α-alanyloxyphenylacetamido, tetrazolylacetamido, α-(4-ethyl-2,3-dioxo-1-piperazinocarbonylamido-p-hydroxyphenylacetamido, hydroxy-protected α-(4-ethyl-2,3-dioxo-1-piperazinocarbonylamido)-p-hydroxyphenylacetamido, o-aminomethylphenylacetamido, amino-protected o- aminomethylphenylacetamido, 2-(5-carboxyimidazole-4-carboxyamido)-2-phenylaceamido, carboxy-protected 2-(5-carboxyimidazole-4-carboxyamido)-2-phenylacetamido, 2-(4-hydroxy-6-methylnicotinamido)-2-(phydroxyphenyl)acetamido, hydroxy-protected 2-(4-hydroxy-6-methylnicotinamido)-2-(p-hydroxyphenyl)acetamido, α-sulfophenylacetamido, 2-(2-amino-4-thiazolyl)-2-(1-carboxy-1-methylethyloxyimino)acetamido, amino- and carboxy-protected 2-(2-amino-4-thiazolyl)-2-(1-carboxy-1-methyloxyimino)acetamido, 2-(6,7-dihydroxy-4-oxo-1-benzopyran-3-carboxyamido)-2-(p-hydroxyphenyl)acetamido, hydroxy-protected 2-(6,7-dihydroxy-4-oxo-1-benzopyran-3-carboxyamido)-2-(p-hydroxyphenyl)acetamido, cyanomethylthioacetamido, 2-aminocarbonyl-2-fluorovinyltioacetamido, amino-protected 2-aminocarbonyl-2-fluorovinylthioacetamido, difluoromethylthioacetamido, α-carboxy-α-(p-hydroxyphenyl)acetamido, hydroxy- and carboxy-protected α-carboxy-α-(p-hydroxyphenyl)acetamido, thienylacetamido, and so on. As examples of said imido group, there may be mentioned phthalimido and so on. As the protective groups for said amino, hydroxyl and carboxyl groups, various known protective groups may be used. To be specific, there may be mentioned benzyl, p-methoxybenzyl, p-nitrobenzyl, 3,4,5-trimethoxybenzyl, 3,5-dimethoxy-4-hydroxybenzyl, 2,4,6-trimethylbenzyl, diphenylmethyl, triphenylmethyl, ditolylmethyl, trityl, piperonyl, naphthylmethyl, 9-anthrylmethyl, tert-butyl, trichloroethyl, and so on.

Examples of $R^3$ include hydrogen atom, hydroxyl group, halogen atoms such as chlorine, bromine, fluorine, etc., lower alkoxyl groups such as methoxy, ethoxy, etc., substituted and unsubstituted vinyl groups such as vinyl, 2,2-dibromovinyl, etc., ethynyl group, lower alkyl groups such as methyl, ethyl, etc., lower alkoxymethyl groups such as methoxymethyl, ethoxymethyl, etc., acetoxymethyl group, carbamoyloxymethyl group, heterocycle-thiomethyl groups such as 1,2,3-triazol-4-ylthiomethyl, 5-methyl-1,3,4-thiadiazol-2-ylthiomethyl, 1-methyltetrazol-5-ylthiomethyl, 1-sulfomethyltetrazol-5-ylthiomethyl, 1-carboxymethyltetrazol-5-ylthiomethyl, 1-(dimethylaminoethyl)tetrazol-5-ylthiomethyl, 1,2,3-thiadiazol-5-ylthiomethyl, 1,2,4-thiadiazol-5-ylthiomethyl, 1-(2-hydroxyethyl)tetrazol-5-ylthiomethyl, etc., 5-methyltetrazol-2-ylmethyl group, 1-methylpyrrolidinomethyl group, pyridiniummethyl group and so on.

Examples of $R^4$ include hydrogen atom, hydroxyl group, halogen atoms such as chlorine, bromine, etc., lower alkoxyl groups such as methoxy, ethoxy, etc., lower acyloxy groups such as formyloxy, acetyloxy, propionyloxy, etc., lower alkylthio groups such as methylthio, ethylthio, etc., heterocycle-thio groups such as 1,3,4-thiadiazol-2-ylthio, 5-methyl-1,3,4-thiadiazol-2-ylthio, 1-methyltetrazol-5-ylthio, etc. and so on.

The symbol n means 0, 1 or 2.

In this specification, the substituent on the phenyl ring of the benzyl or diphenylmethyl group represented by X is exemplified by hydroxyl group, lower alkyl groups such methyl, ethyl, tert-butyl, etc., and lower alkoxyl groups such as methoxy, ethoxy, and so on. Said diphenylmethyl group include substituted or unsubstituted phenyl groups bound together through a methylene chain or a hetero-atom within the molecule. As examples of X groups in the present invention, there may be mentioned p-methoxybenzyl, diphenylmethyl, 3,4,5-trimethoxybenzyl, 3,5-dimethoxy-4-hydroxybenzyl, 2,4,6-trimethylbenzyl, piperonyl, ditolylmethyl, naphthylmethyl, 9-anthrylmethyl, tert-butyl and other groups.

As the β-lactam derivative of general formula (II) used in accordance with the present invention, any of the known derivatives subsumed in the above general formula can be employed.

The phenol compound used in accordance with the present invention is substituted or unsubstituted phenol, and substituents on the phenyl ring may for example be halogen atoms such as chlorine, bromine, etc., lower alkyl groups such as methyl, ethyl, etc., and lower alkoxyl groups such as methoxy, ethoxy, and so on. Examples of such substituted phenols include o-chlorophenol, m-chlorophenol, p-chlorophenol, o-cresol, m-cresol, p-cresol, m-methoxyphenol, and so on.

In the present invention, a β-lactam derivative of general formula (II) is reacted with said phenol compound. Since phenol compound can be used not only as the reactant but also as the solvent, there is no particular limitation on its amount but a suitable amount can be chosen from a broad range. Generally, about 0.5 to 500 weight parts, preferably about 1 to 200 weight parts, can be used relative to each weight part of the β-lactam derivative of general formula (II).

Generally the reaction according to the present invention is preferably conducted in the molten state of said phenol compound and although a solvent is not essential, the reaction may be carried out in the presence of a co-solvent which may be water or an organic solvent such as a halogenated hydrocarbon, e.g. carbon tetrachloride, chloroform, methylene chloride, dichloroethane, trichloroethane, dichloroethylene and so on. However, the use of a large amount of such solvent may interfere with the above reaction and is, therefore, undesirable. The amount of water or said organic solvent is about the same as the amount of phenol compound at most.

The reaction temperature for the above reaction depends on the type of β-lactam derivative of general formula (II), the type of phenol compound, and other factors, and cannot be stated in general terms. However, the reaction temperature is preferably in the range of the minimum temperature at which no solidification of the reaction system takes place to about 100° C. and, for still better results, in the range of the minimum temperature at which no solidification takes place to about 70° C.

In the present invention, a catalyst amount of acid may be present within the reaction system. In this case, depending on types of β-lactam derivatives, the above reaction may be carried out at a lower temperature and in a shorter time. The catalyst amount mentioned above varies with the type of β-lactam derivative and the type of acid but generally speaking, about 0.01 to 100 mole percent, preferably about 0.01 to 50 mole percent, of acid is used relative to the β-lactam derivative of general formula (II). As examples of the acid used as the catalyst, there may be mentioned mineral acids such as hydrochloric acid, sulfuric acid, perchloric acid, phosphoric acid, etc., carboxylic acids such as formic acid, acetic acid, monochloroacetic acid, dichloroacetic acid, trichloroacetic acid, monofluoroacetic acid, difluoroacetic acid, trifluoroacetic acid, etc., sulfonic acids such as benzenesulfonic acid, p-toluenesulfonic acid, methanesulfonic acid, etc., acidic enol compounds such as meldrum's acid, squaric acid, etc., Lewis acids such as aluminum chloride, and solid acids such as acid sodium sulfate, acid potassium sulfate, acid ion exhange resins, and so on.

Following completion of the above reaction, the reaction mixture may be after-treated in the conventional manner to isolate the product β-lactam derivative of general formula (I). For example, either sodium hydrogen carbonate or sodium carbonate and a hydrophobic organic solvent are added to the reaction mixture to extract the β-lactam derivative of general formula (I) into the aqueous layer or crystallized with a poor organic solvent followed by the conventional after-treatment to give the β-lactam derivative of general formula (I) in high yield. Further, by distilling the organic layer, the extraction solvent and the phenol compound can be recovered for re-use.

In the present invention, the R² group containing a protective group for carboxyl, amino or hydroxyl may be removed along with the group X depending on the reaction conditions.

In accordance with the method of the present invention, the protective group can be easily eliminated from the carboxy-protected β-lactam derivative (II). Moreover, since the present invention does not require a large amount of acid unlike in the conventional method, the β-lactam derivative (I) produced by the above reaction is little decomposed, with the result that the β-lactam derivative (I) can be produced in high yield. In addition, because the phenol compound, extraction solvent, etc. can be efficiently recovered, the present invention is economically advantageous. Incidentally, when the moiety

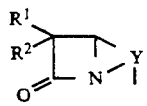

of the βlactam derivative (II) treated according to the present invention has a protected carboxyl group, it may also be eliminated at the same time.

EXAMPLES

The following comparative and working examples are intended to illustrate the present invention in greater detail.

Comparative Example 1

Ten grams of a compound of general formula (II) (where

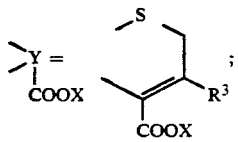

X=p-methoxybenzyl; R¹=H; R²=phenylacetamido; R³=5-methyl-1,3,4-thiadiazol-2-ylthiomethyl), 100 ml of methylene chloride and 6.61 ml of trifluoroacetic acid were admixed and reacted at room temperature for 2 hours. Following completion of the reaction, the methylene chloride and trifluoroacetic acid were distilled off under reduced pressure. To the concentration residue were added 100 ml of 5% aqueous sodium carbonate and 150 ml of ethyl acetate for extraction. The water layer was adjusted to pH 1–2 with hydrochloric acid under ice-cooling and extracted with 300 ml of ethyl acetate. The resulting ethyl acetate layer was concentrated under reduced pressure to give the compound of general formula (I) (where

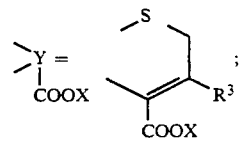

R¹=H; R²=phenylacetamido; R³=5-methyl-1,3,4-thiadiazol-2-ylthiomethyl) in a yield of 61%. The NMR spectrum of this product was in agreement with that of the compound obtained in Example 1 which appears hereinafter. The trifluoroacetic acid distilled off under reduced pressure was trapped with liquid nitrogen and determined by titrimetry. The recovered amount was 3.44 ml.

Comparative Example 2

Ten grams of a compound of general formula (II) (where

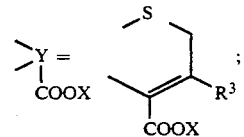

X=p-methoxybenzyl; R¹=H; R²=phenylacetamido; R³=5-methyl-1,3,4-thiadiazol-2-ylthiomethyl), 100 ml of methylene chloride, and 1.32 ml of trifluoroacetic acid were admixed and reacted at room temperature for 5 hours. The reaction did not proceed appreciably.

Comparative Example 3

Ten grams of a compound of general formula (II) (where

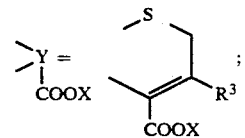

X=p-methoxybenzyl; R¹=H; R²=phenylacetamido; R³=5-methyl-1,3,4-thiadiazol-2-ylthiomethyl) and 100 ml of 99% formic acid were admixed and reacted at room temperature for 3 hours. Following completion of the reaction, the formic acid was distilled off. The concentration residue was after-treated in the same manner as in Comparative Example 1 to give a compound of general formula (I) (where

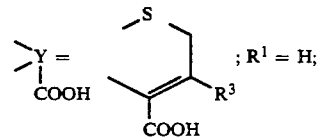

R²=phenylacetamido; R³=5-methyl-1,3,4-thiadiazol-2-ylthiomethyl) in a yield of 55%. The NMR spectrum of this compound was in good agreement with that of the compound produced in Example 1 which appears hereinafter.

Comparative Example 4

In the same manner as described in Tetrahedron Letters 2793 (1979), 1 gram of a compound of general formula (II) (where

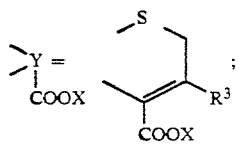

X=p-methoxybenzyl; $R^1$=H; $R^2$=phenylacetamido; $R^3$=5-methyl-1,3,4-thiadiazol-2-ylthiomethyl) was reacted with aluminum chloride to give a compound of general formula (I)

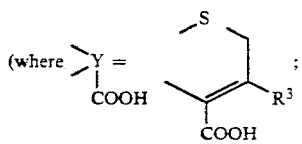

$R^1$=H; $R^2$=phenylacetamido; $R^3$=5-methyl-1,3,4-thiadiazol-2-ylthiomethyl) in a yield of 62%. The NMR spectrum of this compound was in agreement with that of the compound obtained in Example 1 which appears below.

EXAMPLE 1

Two grams of a compound of general formula (II)

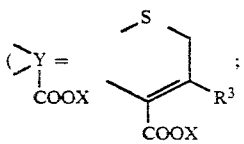

X=p-methoxybenzyl; $R^1$=hydrogen; $R^2$=phenylacetamido; $R^3$=5-methyl-1,3,4-thiadiazol-2-ylthiomethyl) and 6.5 ml of phenol were heated at 60° C. for 3 hours. After the reaction, the reaction mixture was allowed to cool to room temperature and extracted with 19.5 ml of ethyl acetate and 15 ml of 5% aqueous sodium carbonate solution. The water layer was adjusted to pH 1-2 with hydrochloric acid under cooling in an ice bath and extracted with 30 ml of ethyl acetate. The ethyl acetate layer was then concentrated under reduced pressure to give a compound of general formula (I)

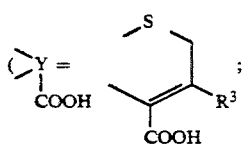

$R^1$=hydrogen; $R^2$=phenylacetamido; $R^3$=5-methyl-1,3,4-thiadiazol-2-ylthiomethyl) in a yield of 85%. The NMR spectrum of the product compound supported its structure.

NMR (acetone-$d_6$), δppm:
2.70 (s, 3H)
3.65 (s, 2H)
3.75 (bs, 2H)
4.35 and 4.53 (ABq, 2H, J=14 Hz)
5.08 (d, 1H, J=5 Hz)
5.78 (dd, 1H, J=5 Hz, 9 Hz)
7.27 (bs, 5H)
7.87 (d, 1H, J=5 Hz)

EXAMPLE 2

Twenty grams of a compound of general formula (II)

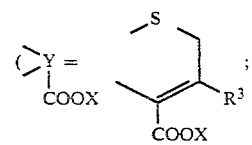

X=p-methoxybenzyl; $R^1$=hydrogen; $R^2$=phenylacetamido; $R^3$=5-methyl-1,3,4-thiadiazol-2-ylthiomethyl) and 40 ml of phenol were mixed and heated at 40° C., followed by addition of 0.25 ml of concentrated hydrochloric acid. The reaction was conducted for 1 hour. After completion of the reaction, the reaction mixture was allowed to cool to room temperature and extracted with 160 ml of methyl isobutyl ketone and 75 ml of 5% aqueous sodium carbonate solution. Under cooling in an ice bath, the aqueous layer was adjusted to pH 1-2 with hydrochloric acid and extracted with 300 ml of ethyl acetate. The ethyl acetate layer was concentrated under reduced pressure to give a compound of general formula (I)

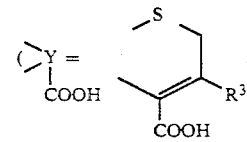

$R^1$=H; $R^2$=phenylacetamido; $R^3$=5-methyl-1,3,4-thiadiazol-2-ylthiomethyl) in a yield of 90%. The NMR spectrum of this product compound was in good agreement with that of the compound obtained in Example 1.

EXAMPLE 3

Twenty grams of a compound of general formula

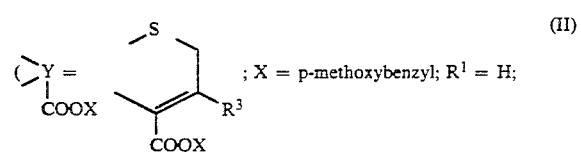

$R^2$=phenylacetamido; $R^3$=1-methyltetrazol-5-ylthiomethyl) and 40 ml of phenol were mixed and heated at 45° C., followed by addition of 85 μl of concentrated hydrochloric acid. The reaction was conducted for 1 hour. After completion of the reaction, the reaction mixture was worked up in the same manner as in Example 2 to give a compound of general formula (I)

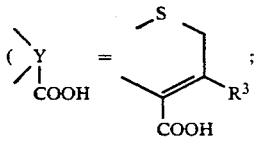

$R^1 = H$; $R^2 =$ phenylacetamido; $R^3 = $ 1-methyltetrazol-5-ylthiomethyl) in a yield of 92%. The NMR spectrum of this product compound supported its structure.

NMR (acetone-$d_6$), δppm:
3.65 (s, 2H)
3.75 (s, 2H)
3.98 (s, 3H)
4.37 (s, 2H)
5.06 (d, 1H, J=5 Hz)
5.74 (dd, 1H, J=5 Hz, 9 Hz)
7.27 (bs, 5H)
7.90 (d, 1H, J=9 Hz)

EXAMPLE 4

Twenty grams of a compound of general formula (II)

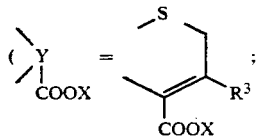

X=diphenylmethyl; $R^1 = H$; $R^2 =$ phenylacetamido; $R^3 = $ 1-methyltetrazol-5-ylthiomethyl) and 40 ml of phenol were mixed and heated at 45° C., followed by addition of 80 μl of concentrated hydrochloric acid. The reaction was conducted for 1 hour. After the reaction, the reaction mixture was worked up in the same manner as in Example 2 to give a compound of general formula (I)

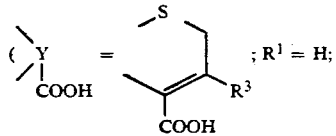

$R^2 =$ phenylacetamido; $R^3 = $ 1-methyltetrazol-5-ylthiomethyl) in a yield of 95%. The NMR spectrum of this product compound was in agreement with that of the compound obtained in Example 3.

EXAMPLE 5

Twenty grams of a compound of general formula

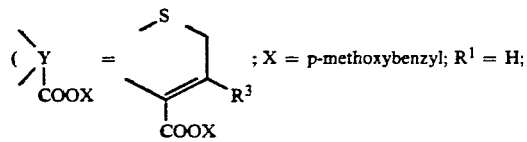

$R^2 =$ phenylacetamido; $R^3 =$ acetoxymethyl) and 40 ml of phenol were mixed and heated at 45° C. To this mixture was added 100 μl of concentrated hydrochloric acid and the reaction was conducted for 1 hour. After completion of the reaction, the reaction mixture was worked up in the same manner as in Example 2 to give a compound of general formula (I)

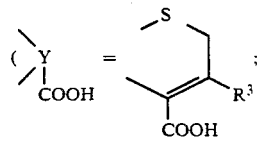

$R^1 = H$; $R^2 =$ phenylacetamido; $R^3 =$ acetoxymethyl) in a yield of 93%. The NMR spectrum of this product compound supported its structure.

NMR (acetone-$d_6$), δppm:
2.04 (s, 3H)
3.52 and 3.61 (ABq, 2H, J=17 Hz)
3.67 (s, 2H)
4.86 and 5.04 (ABq, 2H, J=14 Hz)
5.08 (d, 1H, J=5 Hz)
5.35-6.50 (bs, 3H)
5.80 (dd, 1H, J=5 Hz, 8 Hz)
7.27 (bs, 5H)
7.87 (d, 1H, J=8 Hz)

EXAMPLE 6

The procedure of Example 5 was repeated except that compounds of general formula (II)

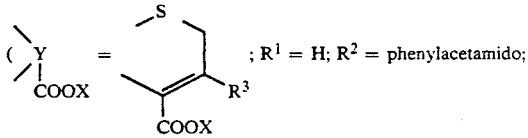

$R^3 =$ acetoxymethyl) having the under-mentioned species of X were used. The resulting product compounds of general formula (I) and their yields were as follows.

The compound of general formula (II) wherein X=3,4,5-trimethoxybenzyl ..... Yield 90%.
The compound of general formula (II) wherein X=3,5-dimethoxy-4-hydroxybenzyl ..... Yield 85%.
The compound of general formula (II) wherein X=2,4,6-trimethylbenzyl ..... Yield 88%.
The compound of general formula (II) wherein X=3,4-methylenedioxybenzyl ..... Yield 90%.
The compound of general formula (II) wherein X=diphenylmethyl ..... Yield 94%.
The compound of general formula (II) wherein ditolylmethyl ..... Yield 96%.
The compound of general formula (II) wherein X=tert-butyl ..... Yield 84%.

EXAMPLE 7

By the same procedure as in Example 3 except that one of the acids mentioned below in Table 1 was used as a catalyst and the reaction conditions specifically indicated in Table 1 were employed, a compound of general formula (II

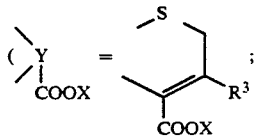

X=p-methoxybenzyl; R¹=H; R²=phenylacetamido; R³=1-methyltetrazol-5-ylthiomethyl) was treated to give the corresponding compound of general formula (I)

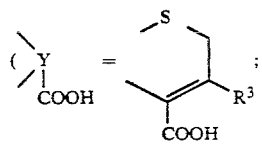

R¹=H; R²=phenylacetamido; R³=1-methyltetrazol-5-ylthiomethyl).

TABLE 1

| Acid | Amount of acid (based on starting compound) (mole %) | Reaction time (hr) | Reaction temperature (°C.) | Yield (%) |
|---|---|---|---|---|
| Sulfuric acid | 2 | 1 | 45 | 96 |
| Perchloric acid | 0.2 | 1 | 45 | 91 |
| Trifluoroacetic acid | 2 | 1.5 | 60 | 89 |
| Trifluoroacetic acid | 10 | 1.5 | 60 | 96 |
| Trifluoroacetic acid | 10 | 1.5 | 60 | 90 |
| p-Toluenesulfonic acid | 5 | 1 | 45 | 94 |
| Methanesulfonic acid | 2 | 1 | 45 | 95 |

EXAMPLE 8

Two-hundred milligrams of a compound of general formula (II)

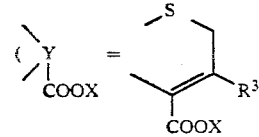

X=p-methoxybenzyl; R¹=H; R²=phenylacetamido; R³=1-methyltetrazol-5-ylthiomethyl) and 0.65 ml of m-chlorophenol were mixed and heated at 60° C. for 1 hour. After completion of the reaction, the reaction mixture was worked up in the same manner as in Example 1 to give a compound of general formula

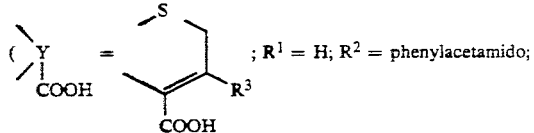

R³=1-methyltetrazol-5-ylthiomethyl) in a yield of 90%. The NMR spectrum of this product compound was in agreement with that of the compound obtained in Example 3.

EXAMPLE 9

Two grams of a compound of general formula (II)

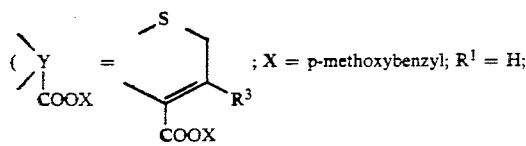

R²=phenylacetamido; R³=1-methyltetrazol-5-ylthiomethyl) and 6.5 ml of m-chlorophenol, and 17 μl of concentrated hydrochloric acid were mixed and reacted at room temperature for 3 hours. After completion of the reaction, the reaction mixture was worked up in the same manner as in Example 2 to give a compound of general formula (I)

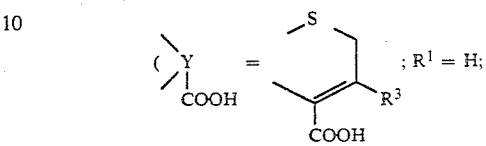

R²=phenylacetamido; R³=1-methyltetrazol-5-ylthiomethyl) in a yield of 89%. The NMR spectrum of this product compound was in agreement with that of the compound obtained in Example 3.

EXAMPLE 10

A compound of general formula (II)

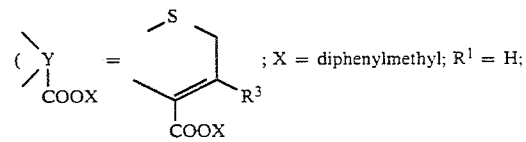

R²=phenylacetamido; R³=acetoxymethyl) was treated in the same manner as in Example 2 to give a compound of general formula (I)

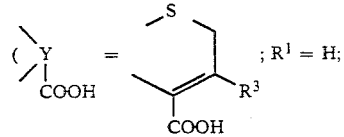

R²=phenylacetamido; R³=acetoxymethyl) in a yield of 93%. The NMR spectrum of this product compound supported its chemical structure.

NMR (CDCl₃), δppm:
2.10 (s, 3H)
3.43 and 3.53 (ABq, 2H, J=19 Hz)
4.57 (s, 2H)
4.92 and 5.08 (ABq, 2H, J=15 Hz)
5.02 (d, 1H, J=5 Hz)
5.87 (dd, 1H, J=5 Hz, 9 Hz)
6.75–7.50 (m, 6H)

EXAMPLE 11

A compound of general formula (II)

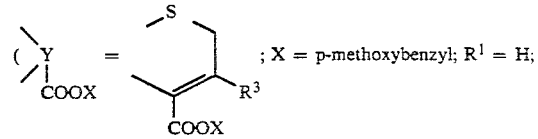

R²=tetrazolylacetamido, R³=5-methyl-1,3,4-thiadiazol-2-ylthiomethyl) was treated in the same manner as in Example 2 to give a compound of general formula (I)

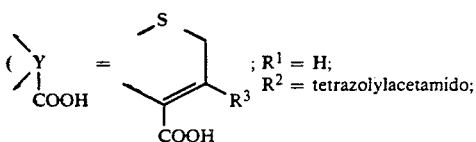
; $R^1 = H$; $R^2 =$ tetrazolylacetamido;

$R^3 = $ 5-methyl-1,3,4-thiadiazol-2-ylthiomethyl) in a yield of 86%. The NMR spectrum of this product compound supported its chemical structure.

NMR (DMSO-$d_6$), δppm:
2.70 (s, 3H)
3.00-5.00 (bs, 1H)
3.63 and 3.76 (ABq, 2H, J=18 Hz)
4.23 and 4.50 (ABq, 2H, J=14 Hz)
5.10 (d, 1H, J=5 Hz)
5.36 (s, 2H)
5.70 (dd, 1H, J=5 Hz, 8 Hz)
9.31 (s, 6H)
9.43 (d, 1H, J=8 Hz)

EXAMPLE 12

A compound of general formula (II)

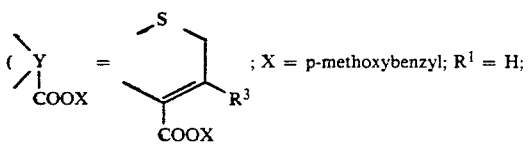
; X = p-methoxybenzyl; $R^1 = $ H;

$R^2 = \alpha$-(tert-butyloxycarbonylamino)phenylacetamido, $R^3 = $ 5-methyl-1,3,4-thiadiazol-2-ylthiomethyl) was treated in the same manner as in Example 2 to give a compound of general formula (I)

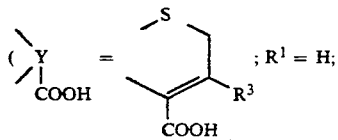
; $R^1 = $ H;

$R^2 = \alpha$-(tert-butyloxycarbonylamino)phenylacetamido, $R^3 = $ 5-methyl-1,3,4-thiadiazol-2-ylthiomethyl) in a yield of 89%. The NMR spectrum of this product compound supported its chemical structure.

NMR (DMSO-$d_6$), δppm:
1.36 (s, 9H)
3.25-4.50 (bs, 1H)
3.56 (bs, 2H)
3.91 (s, 3H)
4.00 (d, 1H, J=8 Hz)
4.22 (bs, 2H)
4.94 (d, 1H, J=5 Hz)
5.26 (d, 1H, J=8 Hz)
5.65 (dd, 1H, J=5 Hz, 8 Hz)
7.10-7.55 (m, 5H)
9.07 (d, 1H, J=8 Hz)

EXAMPLE 13

A compound of general formula (II)

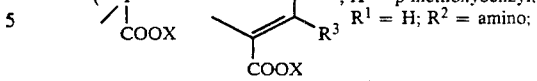
; X = p-methoxybenzyl; $R^1 = $ H; $R^2 = $ amino;

$R^3 = $ 5-methyl-1,3,4-thiadiazol-2-ylthiomethyl) was reacted in the same manner as in Example 2. Following the reaction, ethyl acetate was gradually added with stirring whereupon a compound of general formula (I)

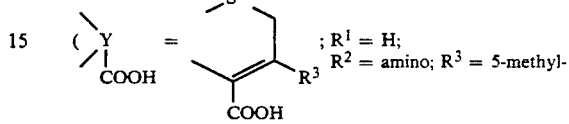
; $R^1 = $ H; $R^2 = $ amino; $R^3 = $ 5-methyl-1,3,4-thiadiazol-2-ylthiomethyl) separated out. The precipitate was recovered by filtration and purified in the conventional manner. The above procedure gave the object compound in a yield of 84%. The NMR spectrum of this product compound was in agreement with the NMR spectrum described in the literature.

EXAMPLE 14

Ten grams of a compound of general formula (II)

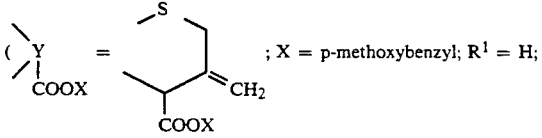
; X = p-methoxybenzyl; $R^1 = $ H;

$R^2 = $ phenylacetamido) and 20 ml of phenol were mixed and heated at 45° C. To this mixture was added 0.37 ml of concentrated hydrochloric acid and the reaction was conducted for 1 hour. After completion of the reaction, the reaction mixture was allowed to cool to room temperature and extracted with 150 ml of ethyl acetate and 100 ml of a saturated aqueous solution of sodium carbonate. Under ice-cooling in an ice bath, the aqueous layer was adjusted to pH 1-2 with hydrochloric acid and extracted with 200 ml of ethyl acetate. The ethyl acetate layer was concentrated under reduced pressure to give a compound of general formula (I)

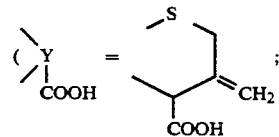
;

$R^1 = $ H; $R^2 = $ phenylacetamido) in a yield of 85%. The NMR spectrum of this product compound supported its chemical structure.

NMR (acetone-$d_6$), δppm:
3.35 and 3.69 (ABq, 2H, J=14 Hz)
3.65 (s, 2H)
5.08 (s, 1H)
5.28 (s, 2H)
5.34 (d, 1H, J=5 Hz)
5.57 (dd, 1H, J=5 Hz, 9 Hz)
7.05-7.45 (m, 5H)
7.75 (d, 1H, J=9 Hz)

EXAMPLE 15

A compound of general formula (II)

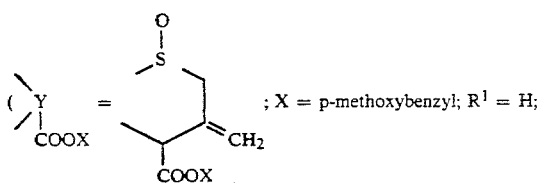
; X = p-methoxybenzyl; R$^1$ = H;

R$^2$=phenoxyacetamido) was treated in the same manner as in Example 14 to give a compound of general formula (I)

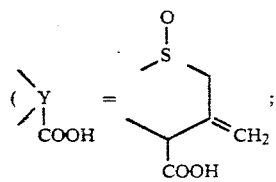

R$^1$ = H; R$^2$ = phenoxyacetamido)

in a yield of 87%. The NMR spectrum of this product compound supported its chemical structure.
NMR (DMSO-d$_6$/CLCl$_3$) δppm:
3.80 (s, 2H)
4.53 (s, 2H)
5.05 (s, 1H)
5.10 (d, 1H, J=5 Hz)
5.40 (s, 1H)
5.70 (s, 1H)
5.90 (dd, 1H, J=5 Hz, 9 Hz)
6.85-7.50 (m, 5H)
9.65 (d, 1H, J=9 Hz)

EXAMPLE 16

A compound of general formula (II)

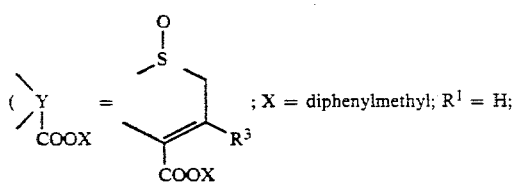
; X = diphenylmethyl; R$^1$ = H;

R$^2$ = thiolacetamido; R$^3$ = 1-methyltetrazol-5-ylthiomethyl) was treated in the same manner as in Example 2 to give a compound of general formula (I)

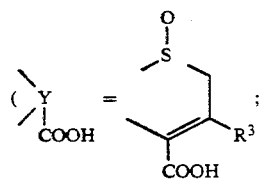

R$^1$=H; R$^2$=thiolacetamido; R$^3$=1-methyltetrazol-5-ylthiomethyl) in a yield of 89%. The NMR spectrum of this product compound supported its chemical structure.
NMR (acetone-d$_6$/methanol-d$_4$) δppm:
3.84 and 4.37 (ABq, 2H, J=16 Hz)
3.92 (s, 3H)
4.01 (s, 2H)
4.30 and 4.73 (ABq, 2H, J=14 Hz)
4.60 (d, 1H, J=5 Hz)
5.56 (d, 1H, J=5 Hz)
6.85-7.45 (m, 3)

EXAMPLE 17

A compound of general formula (II)

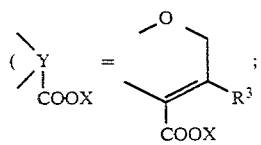

X = diphenylmethyl; R$^1$ = methoxy;

R$^2$=α-(p-methoxybenzyloxycarbonyl)-phenylacetamido; R$^3$=1-methyltetrazol-5-ylthiomethyl) was treated in the same manner as in Example 14 to give a compound of general formula (I)

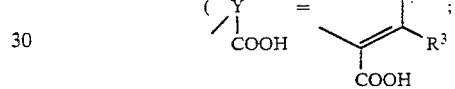

R$^1$=methoxy; R$^2$=α-carboxyphenylacetamido; R$^3$=1-methyltetrazol-5-ylthiomethyl) in a yield of 85%. The NMR spectrum of this product compound was in agreement with that described in the literature.

EXAMPLE 18

A compound of general formula (II)

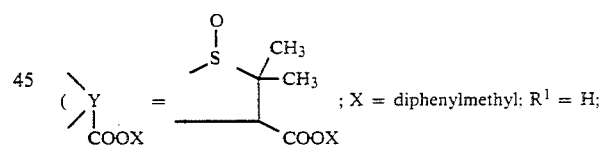
; X = diphenylmethyl; R$^1$ = H;

R$^2$=phenylacetamido) was treated in the same manner as in Example 2 to give a compound of general formula (I)

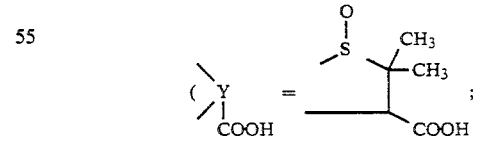

R$^1$ = H; R$^2$ = phenylacetamido)

in a yield of 86%. The NMR spectrum of this product compound was in agreement with that described in the literature.

EXAMPLE 19

A compound of general formula (II)

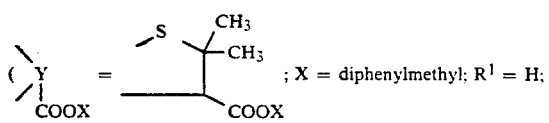

R²=phenylacetamido) was treated in the same manner as in Example 2 to give a compound of general formula (I)

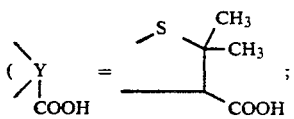

R¹ = H; R² = phenylacetamido)

in a yield of 90%. The NMR spectrum of this product compound was in agreement with that described in the literature.

EXAMPLE 20

A compound of general formula (II)

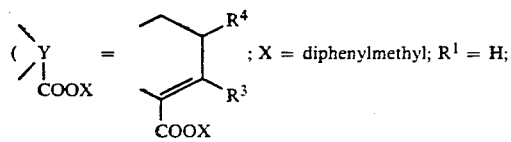

R²=thiolacetamido, and R³ and R⁴ each is H) was treated in the same manner as in Example 2 to give a compound of general formula (I)

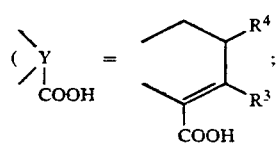

R¹=H; R²=thiolacetamido; R³ and R⁴ each is H) in yield of 94%. The NMR spectrum of this product compound was in agreement with that described in the literature.

EXAMPLE 21

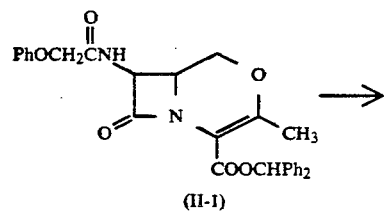

A compound of the formula (II-1) was treated in the same manner as in Example 14, giving a compound of the formula (I-1) in a yield of 87%. The NMR spectrum of the obtained compound was in agreement with that set forth in the literature.

EXAMPLE 22

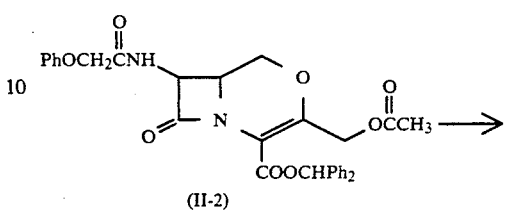

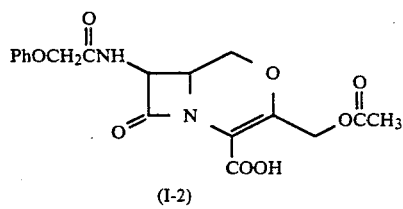

A compound of the formula (II-2) was treated in the same manner as in Example 14, producing a compound of the formula (I-2) in a yield of 85%. The NMR spectrum of the obtained compound was in agreement with that set forth in the literature.

EXAMPLE 23

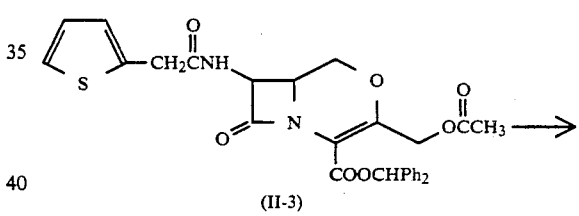

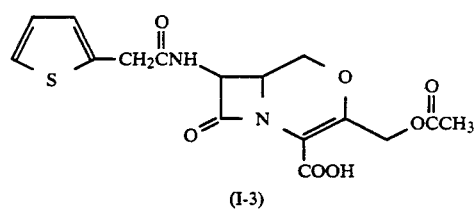

A compound of the formula (II-3) was treated in the same manner as in Example 14, giving a compound of the formula (I-3) in a 90% yield. The NMR spectrum of the obtained compound was in agreement with that set forth in the literature.

EXAMPLE 24

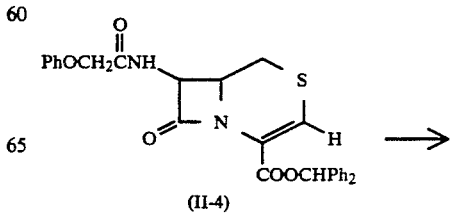

-continued

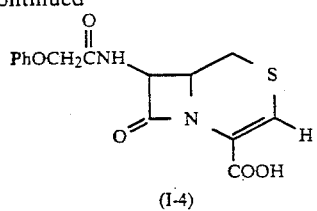

(I-4)

A compound of the formula (II-4) was treated in the same manner as in Example 14, giving a compound of the formula (I-4) in a 80% yield. The NMR spectrum of the obtained compound was in agreement with that set forth in the literature.

EXAMPLE 25

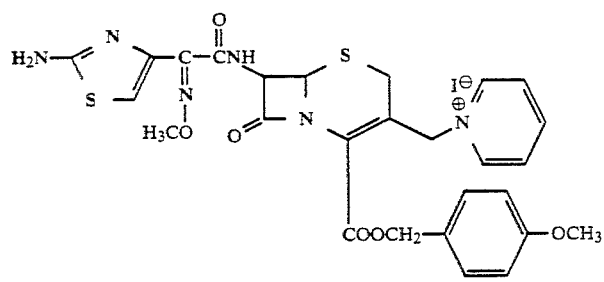

(II-5)

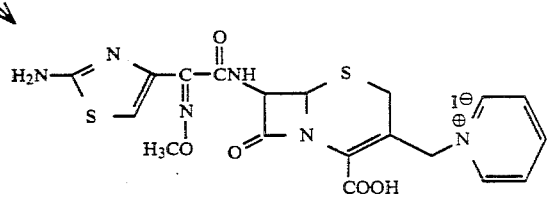

(I-5)

A 5 g quantity of a compound of the formula (II-5) was added to 20 ml of phenol heated at 45° C. and 0.12 ml of 35% HCl was added thereto. The mixture was subjected to reaction with stirring at 45° C. for 1 hour. After completion of the reaction, the mixture was cooled to room temperature and 100 ml of ethyl acetate was added thereto with stirring, giving a precipitate of compound of the formula (I-5). The precipitate was collected by filtration, washed with acetone and dried, giving the compound of the formula (I-5) in a 86% yield. The NMR spectrum of the obtained compound was in agreement with that set forth in the literature.

EXAMPLE 26

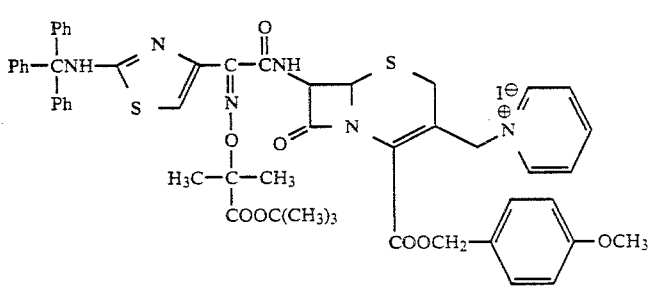

(II-6)

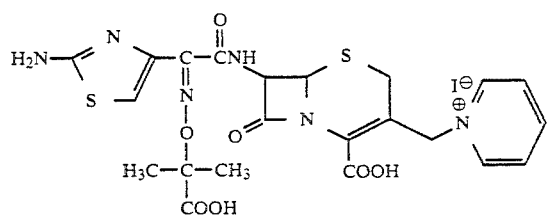

(I-6)

A 8.5 g quantity of a compound of the formula (II-6) was added to 34 ml of phenol heated at 45° C. and 1.7 ml of 35% hydrochloric acid was added thereto. the mixture was subjected to reaction with stirring at 45° C. for 1 hour. After completion of the reaction, the mixture was cooled to room temperature and 200 ml of isopropyl ether was added thereto with stirring, giving a precipitate of compound of the formula (I-6). The precipitate was collected by filtration, washed with isopropyl ether and dried to give a compound of the formula (I-6) in a yield of 87%. The NMR spectrum of this product compound was in agreement with that described in the literature.

EXAMPLE 27

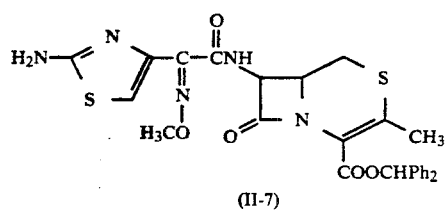
(II-7)

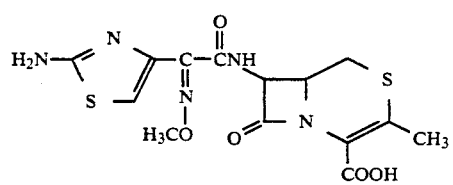
(I-7)

A compound of the formula (II-7) was treated in the same manner as in Example 25, giving a compound of the formula (I-7) in a 92% yield. The NMR spectrum of the obtained compound was in agreement with that set forth in the literature.

EXAMPLE 28

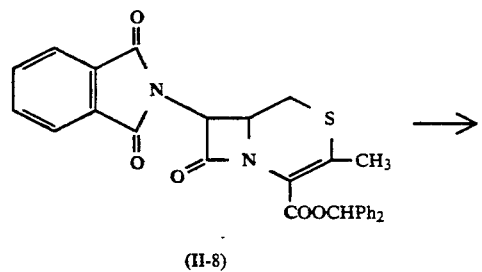
(II-8)

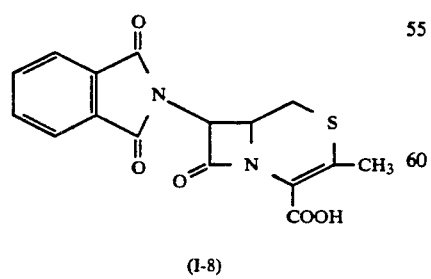
(I-8)

A compound of the formula (II-8) was treated in the same manner as in Example 14, producing a compound of the formula (I-8) in a 93% yield.

NMR (DMSO-$d_6$) δppm:
2.15 (s, 3H)
3.24 (m, 2H)
4.06 (m, 1H)
5.80 (d, 1H, J=4.94 Hz)
7.91 (m, 4H)

EXAMPLE 29

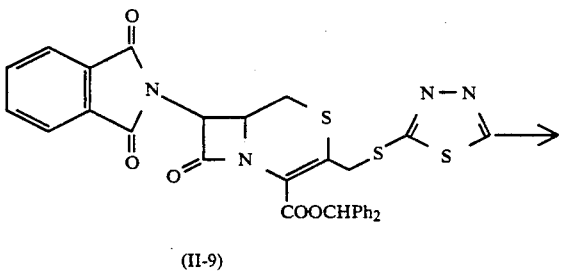
(II-9)

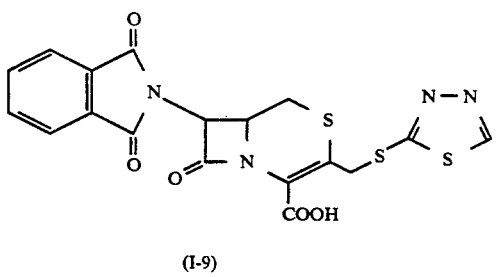
(I-9)

A compound of the formula (II-9) was treated in the same manner as in Example 14, giving a compound of the formula (I-9) in a 90% yield.

NMR (DMSO-$d_6$) δppm:
3.20 (m, 2H)
4.14 (m, 1H)
4.58 (ABq, 2H, J=14.3 Hz)
5.95 (d, 1H, J=5.22 Hz)
7.91 (m, 4H)
9.55 (s, 1H)

We claim:

1. A method of producing a β-lactam derivative represented by the formula (I):

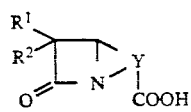 (I)

wherein $R^1$ is a hydrogen atom, a lower alkoxy group or a formamido group; $R^2$ is a hydrogen atom, a halogen atom, an amino group, an amido group or an imido group;

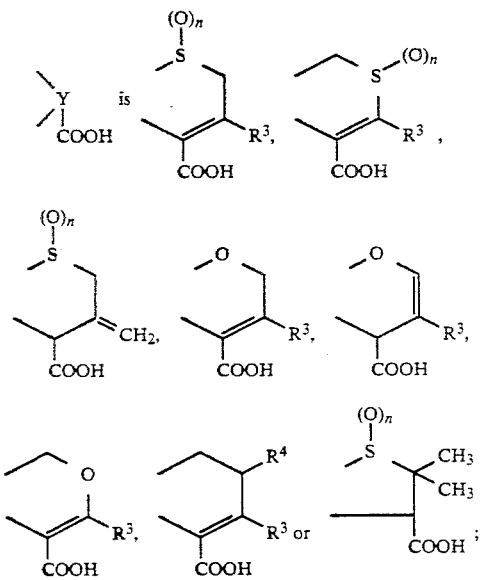 is $R^3$ is a hydrogen atom, a hydroxyl group, a halogen atom, a lower alkoxyl group, a vinyl group unsubstituted or substituted by one or two halogen atoms bonded to the same carbon atom of said vinyl group, a lower alkoxymethyl group, acetoxymethyl group, carbamoyloxymethyl group, a heterocycle-thiomethyl group wherein the heterocycle is a five-membered heteroaromatic ring containing in the ring up to four heteroatoms selected from the group consisting of sulfur and nitrogen, said heteroaromatic ring being unsubstituted or substituted by a substitutent selected from the group consisting of methyl and ethyl, said substitutent being optionally substituted with a group selected from the group consisting of —SO₃H, —COOH, —OH, —NH₂, —NHCH₃, and —N(CH₃)₂, 5-methyltetrazol-2-ylmethyl group, 1-methylpyrrolidinomethyl group or pyridiniummethyl group; $R^4$ is a hydrogen atom, a hydroxyl group, a halogen atom, a lower alkoxyl group, a group —OOCR wherein R is a lower alkyl group, a lower alkylthio group or a heterocycle-thio group wherein the heterocycle is as defined above; and n is 0, 1 or 2, said method consisting essentially of the step of reacting at a temperature in the range from room temperature to 100° C. a β-lactam derivative represented by the formula (II):

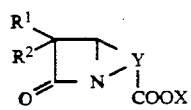 (II)

wherein $R^1$ and $R^2$ are as defined above,

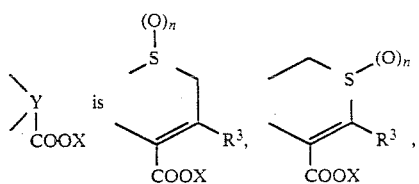

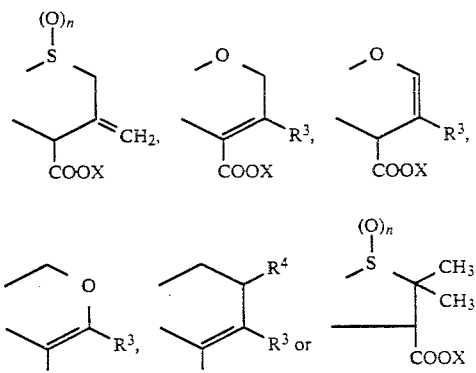

and X is selected from the group consisting of a benzyl group having a hydroxyl group, a lower alkyl group or a lower alkoxy group as a phenyl ring substitutent, a diphenylmethyl group, a diphenylmethyl group having a hydroxyl group, a lower alkyl group or a lower alkoxy group as a phenyl ring substitutent, or tert-butyl, with a phenol in a reaction system which consists essentially of said β-lactam derivative of formula (II) and said phenol.

2. A method of producing a β-lactam derivative represented by the formula (I):

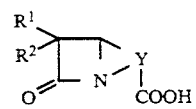 (I)

wherein $R^1$ is a hydrogen atom, a lower alkoxy group or a formamido group; $R^2$ is a hydrogen atom, a halogen atom, an amino group, an amido group or an imido group;

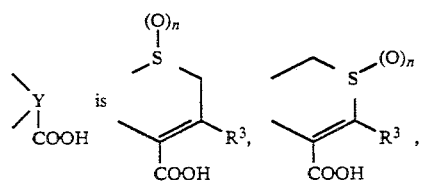

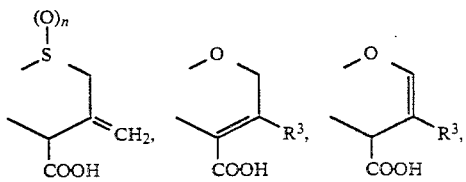

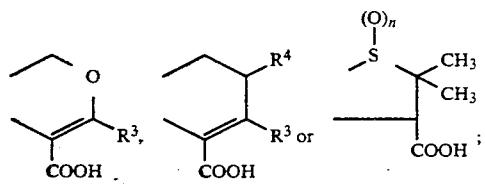

R³ is a hydrogen atom, a hydroxyl group, a halogen atom, a lower alkoxyl group, a vinyl group unsubstituted or substituted by one or two halogen atoms bonded to the same carbon atom of said vinyl group, a lower alkoxymethyl group, acetoxymethyl group, carbamoyloxymethyl group, a heterocycle-thiomethyl group wherein the heterocycle is a five-membered heteroaromatic ring containing in the ring up to four heteroatoms selected from the group consisting of sulfur and nitrogen, said heteroaromatic ring being unsubstituted or substituted by a substitutent selected from the group consisting of methyl and ethyl, said substitutent being optionally substituted with a group selected from the group consisting of —SO₃H, —COOH, —OH, —NH₂, —NHCH₃, and —N(CH₃)₂, 5-methyltetrazol-2-ylmethyl group, 1-methylpyrrolidinomethyl group or pyridiniummethyl group; R⁴ is a hydrogen atom, a hydroxyl group, a halogen atom, a lower alkoxyl group, a group —OOCR wherein R is a lower alkyl group, a lower alkylthio group or a heterocycle-thio group wherein the heterocycle is as defined above; and n is 0, 1 or 2, said method consisting essentially of the step of reacting at a temperature in the range from room temperature 100° C. a β-lactam derivative represented by the formula (II):

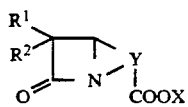
(II)

wherein R¹ and R² are as defined above,

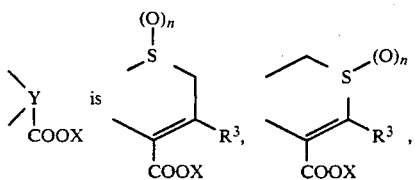
is

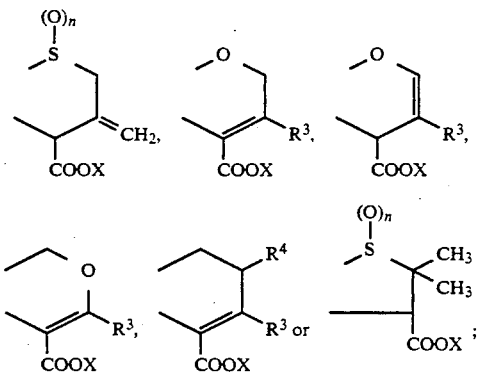

and X is selected from the group consisting of a benzyl group having a hydroxyl group, a lower alkyl group or a lower alkoxy group as a phenyl ring substitutent, a diphenylmethyl group, a diphenylmethyl group having a hydroxyl group, a lower alkyl group or a lower alkoxy group as a phenyl ring substitutent, or tert-butyl, with a phenol in a reaction system which consists essentially of said β-lactam derivative of the formula (II), said phenol, and an acid.

3. The method according to claim 1 or 2 wherein said phenol compound is at least one member selected from the group consisting of phenol, o-chlorophenol, m-chlorophenol, p-chlorophenol, o-cresol, m-cresol, p-cresol and m-methoxyphenol.

4. The method according to any of claims 1 or 2 wherein about 0.5 to 500 weight parts of said phenol compound is reacted with the starting material β-lactam derivative.

5. The method according to claim 1 or 2, wherein said phenol compound is phenol.

6. The method according to claim 1 or 2, wherein said phenol compound is selected from the group consisting of o-cresol, m-cresol and p-cresol.

* * * * *

UNITED STATES PATENT AND TRADEMARK OFFICE
CERTIFICATE OF CORRECTION

PATENT NO. : 5,070,194
DATED : December 3, 1991
INVENTOR(S) : Michio SASAOKA et al It is certified that error appears in the above-identified patent and that said Letters Patent is hereby corrected as shown below:

On the cover page, after Item [22], the following should appear:

-- [30]   Foreign Application Priority Data
 .  May 17, 1985   [JP]   Japan . . . . . . . 106274/1985

Signed and Sealed this

First Day of August, 1995

Attest:

BRUCE LEHMAN

Attesting Officer     Commissioner of Patents and Trademarks